United States Patent [19]
Varney

[11] Patent Number: 5,078,713
[45] Date of Patent: Jan. 7, 1992

[54] CRYOSURGICAL PROBE

[75] Inventor: Kelvin J. Varney, Andover, England

[73] Assignee: Spembly Medical Limited, Andover, England

[21] Appl. No.: 444,027

[22] Filed: Nov. 30, 1989

[30] Foreign Application Priority Data

Dec. 1, 1988 [GB] United Kingdom ............... 8828062

[51] Int. Cl.⁵ .............................................. A61B 17/36
[52] U.S. Cl. .......................................... 606/23; 606/22
[58] Field of Search ............................ 606/21, 22, 23; 128/400, 401

[56] References Cited

U.S. PATENT DOCUMENTS

| | | | |
|---|---|---|---|
| 3,266,492 | 8/1966 | Steinberg | 606/23 |
| 3,272,203 | 9/1966 | Chato | 606/21 |
| 3,421,508 | 1/1969 | Nestrock | 606/21 |
| 3,800,552 | 4/1974 | Sollami et al. | 606/23 |
| 3,913,581 | 10/1975 | Ritson et al. | 606/23 |
| 3,971,383 | 7/1976 | Van Geruen | 606/24 |
| 4,015,606 | 4/1977 | Mitchiner et al. | 606/23 |
| 4,946,460 | 8/1990 | Merry et al. | 606/21 |

FOREIGN PATENT DOCUMENTS 1011121  4/1983  U.S.S.R. ............................. 606/23

Primary Examiner—Lyle L. Howell
Assistant Examiner—Scott R. Ahers
Attorney, Agent, or Firm—Stanley J. Price, Jr.

[57] ABSTRACT

A cryosurgical probe having a probe head which is cooled by Joule-Thomson cooling, and is then used to freeze bodily tissue during a surgical procedure. A steerable catheter is connected between the probe head and a probe handle to enable the probe head to be guided with safety and precision along arteries of the body to the target area.

3 Claims, 2 Drawing Sheets

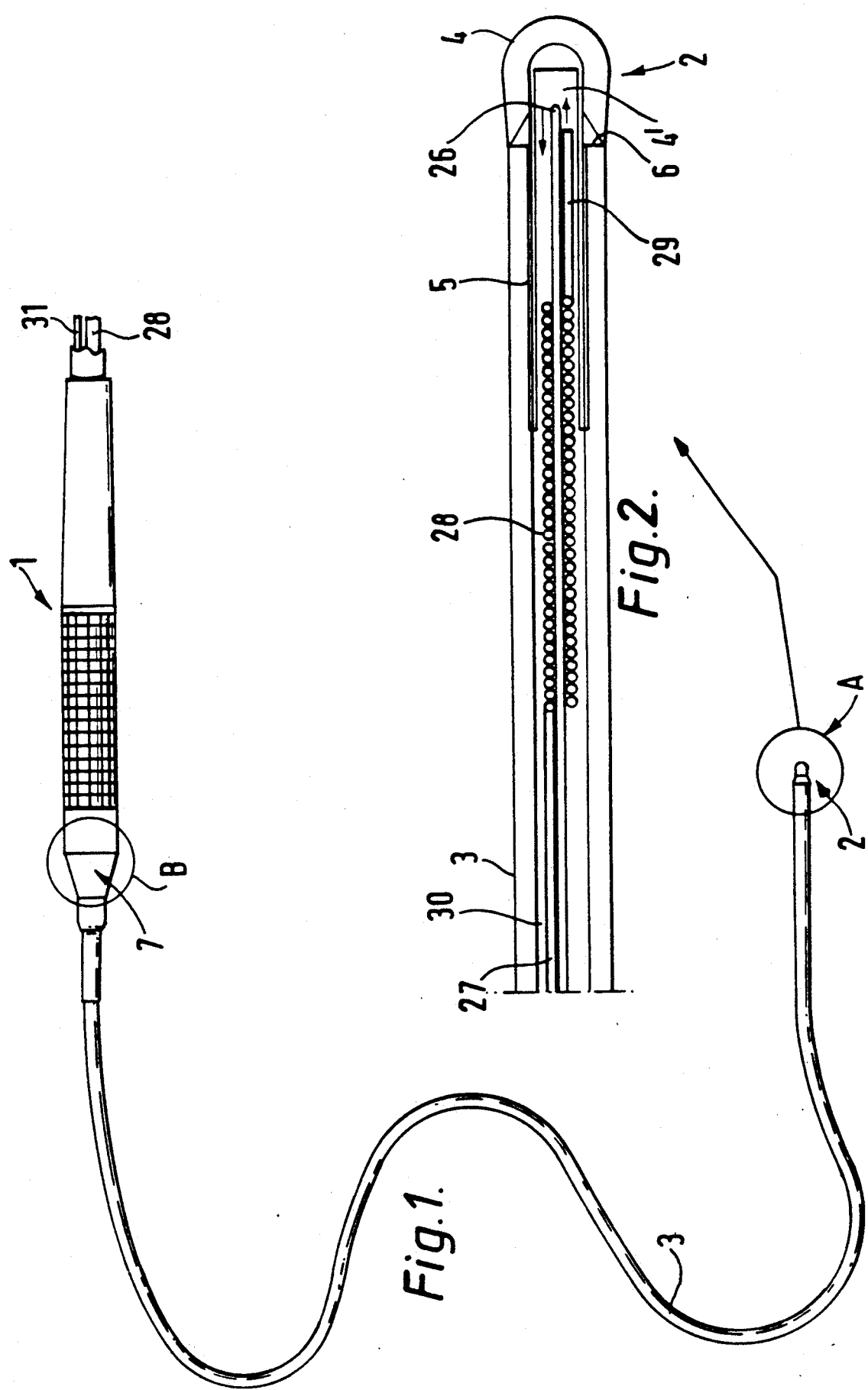

CRYOSURGICAL PROBE

BACKGROUND OF THE INVENTION

1. Field of the Invention

The present invention relates to a cryosurgical probe and in particular to a cryosurgical catheter probe for percutaneous employment in a surgical procedure.

2. Description of the Prior Art

Cryosurgical probes are presently in use for freezing body tissue to a degree sufficient to produce a temporary reversible block of electrical conduction through tissue, an inflammatory response, cryo-adhesion or cryo-necrosis. The probe tip is cooled by passing refrigerant (liquid, gas or vapor) at high pressure through a restriction at the tip to cause a loss of pressure with consequent loss of heat and rapid cooling. This phenomenon is commonly known as the Joule-Thomson effect, and is used significantly to reduce the temperature on the exterior surface of the probe tip which is then used for the freezing process.

Such probes are extensively used to freeze external body tissue, and surgically exposed tissue for example in the treatment of skin cancer. However an extension of the use of cryogenic probes for the treatment of internal organs, such as the heart, is now under further active consideration.

In the application of a cryogenic probe to treat the human heart, for example to freeze and destroy aberrant conductive heart tissue, it is necessary to maneuver the probe along the femoral artery from a position in the groin to direct the tip at the end of the probe to the area to be treated.

To achieve this purpose the probe has to be given a steerable capability to enable the surgeon readily to manipulate the probe along the artery to its final destination which necessarily involves a certain amount of twisting or torque being applied over a constantly increasing distance as between the chosen entry to the artery and the probe tip.

SUMMARY OF THE INVENTION

It is an object of the invention to provide a cryogenic probe for percutaneous use which can be guided with safety and precision along arteries of the body to the target area.

According to the invention there is provided a cryosurgical probe comprising a probe head for applying to bodily tissue to be frozen and provided with a cavity, catheter means connected to the probe head for guiding the probe head along an artery of the body, first and second passageways in the catheter leading to said cavity of the probe head, and a restriction in the first passageway such that a refrigerant at high pressure passed therealong suffers cooling after passage through the restriction to cause a reduction in temperature of the probe head, said second passageway being provided to exhaust the cooled refrigerant from said cavity.

Advantageously the probe is provided with a probe handle coupled to the catheter and containing an internal chamber for directing the primary refrigerant flow through the first passageway from a refrigerant inlet, and the exhaust refrigerant flow from the second passageway through a refrigerant outlet.

The first passageway is preferably in the form of a fine stainless steel tube extending axially of the catheter means between the internal chamber in the probe handle and the cavity in the probe head.

A lead wire may be positioned along the length of the catheter means for supporting the stainless steel tube. At the probe head end of the catheter means, the steel tube of the first passageway is coiled around the lead wire to form a heat exchanger. As and cooler exhaust refrigerant in the second passageway formed between the steel tube and the internal walls of the catheter means passes over the coils of the first passageway wound around the lead wire which may be a thermocouple, the cooler exhaust refrigerant further cools the incoming refrigerant in the first passageway to further lower the temperature at the tip of the probe.

In this way some of the waste energy in the exhaust refrigerant may be recovered whereby to improve probe performance especially since the probe may be used to freeze organs with a perfuse warm blood flow.

Advantageously the lead wire may comprise a thermocouple to monitor the tip temperature.

These and other objects of the present invention will be more completely disclosed and described in the following specification, the accompanying drawings and the appended claims.

BRIEF DESCRIPTION OF THE DRAWINGS

The invention will now be described by way of example with reference to the accompanying drawings where FIG. 1 is a view in elevation of a cryogenic catheter probe according to the invention;

FIG. 2 is a view in detail at A of FIG. 1 showing the probe head and catheter connection thereto.

DESCRIPTION OF THE PREFERRED EMBODIMENTS

Figure 3:
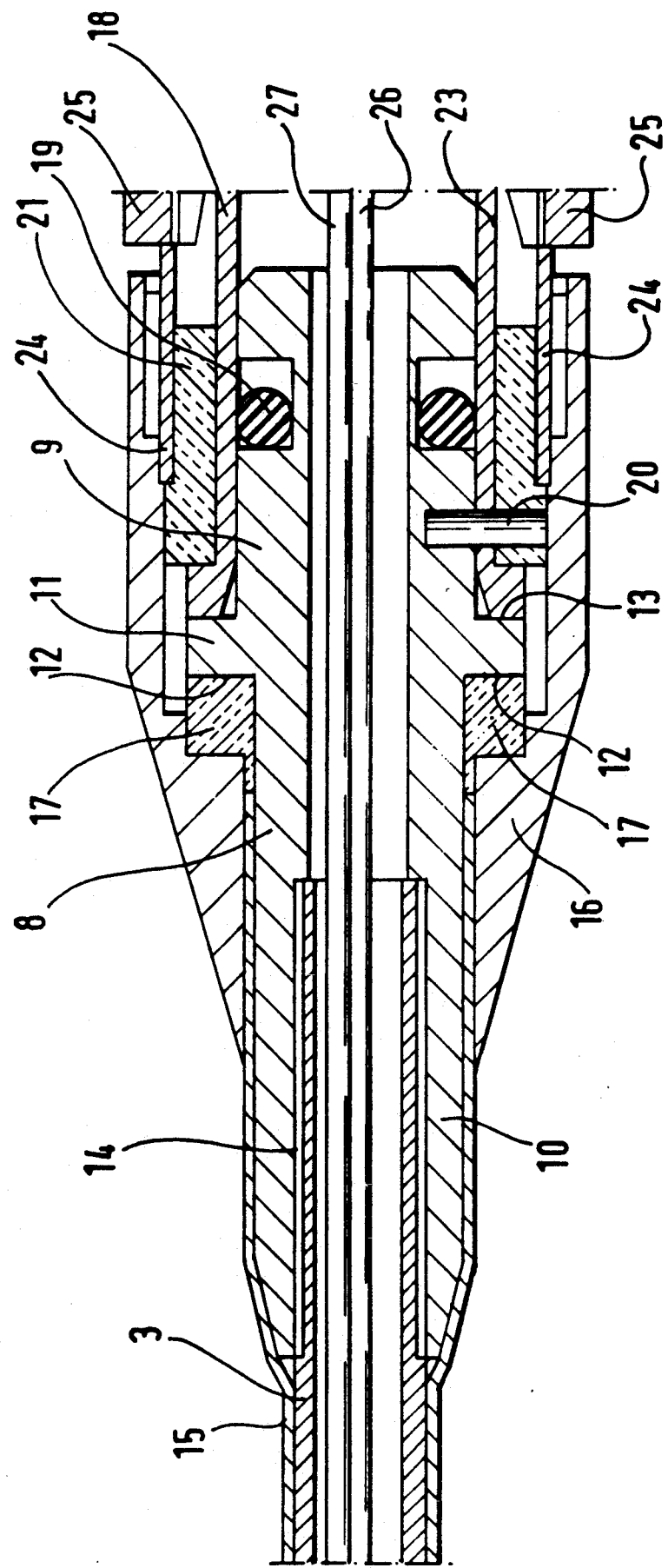
FIG. 3 is a view in detail at B of FIG. 1 showing the probe handle and catheter connection thereto.

The probe shown in the drawings comprises a probe handle 1, a probe head 2, and a catheter 3 connected at one end to the handle 1 and at the other end to the head 2.

In the example illustrated, the catheter 3 is an angiographic catheter made up of an inner woven Dacron (RTM) core and an outer polyurethane build-up such catheters being available but not exclusively from the Systems Division of the USCI Corporation.

The probe head 2 is a tubular member having a semispherical tip 4, with grooves 5 formed in the inner diameter of catheter 3 adjacent tip 4. Other tip 4 shapes may be employed depending on the anatomical procedure in respect of which the probe is being used.

The head 2 is secured in one end of the catheter 3 by means of the grooves 5 and epoxide adhesive engaging the inner walls of the core of the catheter 2, with the tip 4 protruding from the end of the catheter as illustrated in FIG. 2.

A bead of adhesive 6 is used to blend the tip 4 to complete the assembly of the head 2 to the catheter 3, and to allow smooth insertion into the artery when in use.

The other end of the catheter 3 is connected to a probe handle 1 by means of a catheter connection 7.

The catheter connection, see FIG. 3, comprises a central connector element 8 having a head section 9 and a depending tail section 10 separated by a peripheral flange 11 forming forward and rearward peripheral ledges 12 and 13. The depending tail section 10 has a threaded bore 14.

When connecting the catheter 3 to the connector element 8 a bonding agent such as epoxide adhesive is first applied over the catheter 3. The catheter 3 is then screwed into the bore 14 to provide mechanical retention.

Heat shrink tubing 15 is applied around the catheter 3 and tail section 10 to act as a form of strain relief when bending the joint and when torque is applied to steer the catheter 3 with the probe head 2 along an artery of the body.

A tapered cap 16 is secured around the connector element 8 and over the tubing 15.

The peripheral flange 11 is thermally isolated from the tapered cap 16 by insulator ring 17, held against the ledge 12 of flange 11, and the surface of the tail section 10 of the element 8, and abutting the heat shrink tubing 15.

The head section 9 is pneumatically sealed in a refrigerant chamber 18 formed in the handle 1 by 'O' ring 19 and mechanically retained with a pin 20. The handle 1 is thermally isolated from the chamber 18 by insulator 21 held between wall 22 of cap 16 and the wall 23 of chamber 18.

The tapered cap 16 is attached to a threaded extension 24 of the main body 25 of handle 1 acting as a secondary retention of connector element 8 in the gas chamber 18. A part of insulator 21 is interposed between the threaded extension 24 and the wall 23 of the chamber 18.

A thermocouple 26, see FIGS. 2 and 3, doubling as a brace to maintain axial alignment of hypodermic tube 27 extends axially along the catheter 3 from the handle 1 to a position protruding a short distance into the probe head 2.

A stainless steel hypodermic tube 27 for delivery of a refrigerant at high pressure to the probe head 2, extends axially of the catheter 3. The tube 27 is linked within the chamber 18 to a refrigerant inlet (not shown) ultimately connected to a refrigerant source (not shown).

As illustrated in FIG. 2, tube 27 is positioned against the thermocouple 26 and coiled around the same near the probe head 2, over a predetermined extent to form a heat exchanger section 28 between the coils of tube 27 and cooled exhaust refrigerant whose purpose will be explained further hereinbelow.

A short rectilinear length 29 of the tube 27 leads from the heat exchanger section 28 to terminate in the cavity 4' of the tip 4. The tube length 29 is provided with a restriction (not shown).

The axially extending space between the thermocouple 26 and tube 27 and the inner walls of the catheter 3, forms a passageway 30 for exhaust refrigerant passing from the cavity 4' to an exhaust refrigerant outlet at the rear end of the handle 6.

In operation high pressure liquified gas such as CO or NO is delivered to the cavity 4' of the probe tip 4 by way of the tube 27. As the refrigerant passes through the restriction formed in the tube length 29 it undergoes Joule-Thomson cooling whereby to effect a significant reduction in temperature on the semi-spherical tip 4 of the probe head 2.

The exhaust refrigerant is then passed to the outlet through the passageway 30 and as it does so passes over the heat exchanger section 28 whereby it cools the incoming refrigerant passing through the heat exchanger coils of tube 27 coiled around thermocouple 26, thus reducing the tip temperature still further by reducing the temperature of incoming refrigerant in tube 27.

Freezing of the tip 4 as described above, is carried out after insertion of the probe head 2 to the required target area within the human body, the flexible catheter 3 permitting the head 2 to be steered to the target area without excessive strain being imposed upon the connections between the catheter and handle 1, and probe head 4.

According to the provisions of the Patent Statutes, I have explained the principle, preferred construction and mode of operation of my invention and have illustrated what I now consider to represent its best embodiments. However, it should be understood that, within the scope of the appended claims, the invention may be practiced otherwise than as specifically illustrated and described.

I claim:

1. A cryosurgical probe comprising a probe head for applying a bodily tissue to be frozen and provided with a cavity, flexible catheter means connected to said probe head for guiding said probe head along an artery of the body, first and second passageways in said catheter means leading to said cavity of said probe head, a restriction in said first passageway such that a refrigerant at high pressure passed therealong suffers cooling after passage through the restriction to cause a reduction in temperature in said probe head, said second passageway being provided to exhaust the cooled refrigerant from said cavity, a bracing support means positioned axially along the length of said catheter means for supporting said first passageway, said first passageway having several coils adjacent said probe end of said cathether means, said coils forming a heat exchanger between warmer primary refrigerant in said first passageway and cooler exhaust refrigerant in said second passageway, and said bracing support means including a thermocouple for monitoring the temperature of said tip of said probe head.

2. The probe as set forth in claim 1 wherein a probe handle is coupled to said catheter means, said probe handle having an internal chamber for directing primary refrigerant flow through said first passageway from a refrigerant inlet, and exhaust refrigerant flow from said second passageway through a refrigerant outlet.

3. The probe as set forth in claim 1, wherein said first passageway is in the form of a fine stainless steel tube extending axially of said catheter means between said internal chamber and said cavity.

* * * * *